US005777153A

United States Patent [19]
Lin et al.

[11] Patent Number: 5,777,153
[45] Date of Patent: Jul. 7, 1998

[54] CATIONIC LIPIDS

[75] Inventors: Kuei-Ying Lin, Fremont; Jason G. Lewis, San Francisco; Mark D. Matteucci; Richard W. Wagner, both of Burlingame, all of Calif.

[73] Assignee: Gilead Sciences, Inc., Foster City, Calif.

[21] Appl. No.: 273,045

[22] Filed: Jul. 8, 1994

[51] Int. Cl.[6] .................. C07C 271/20; C07C 237/06; C07C 237/22
[52] U.S. Cl. .................. 560/158; 560/159; 564/157; 564/159; 536/22.1
[58] Field of Search ................... 564/157, 159; 560/158, 159; 536/22.1

[56] References Cited

U.S. PATENT DOCUMENTS

| | | | |
|---|---|---|---|
| 2,426,891 | 9/1947 | Lynch | 260/561 |
| 4,548,955 | 10/1985 | Okahata et al. | 521/53 |
| 5,171,678 | 12/1992 | Behr et al. | 435/172.3 |
| 5,279,833 | 1/1994 | Rose | 424/450 |
| 5,283,185 | 2/1994 | Epand et al. | 435/172.3 |
| 5,583,020 | 12/1996 | Sullivan | 435/172.3 |
| 5,614,503 | 3/1997 | Chaudhary et al. | 544/44 |

FOREIGN PATENT DOCUMENTS

| | | | |
|---|---|---|---|
| 0 348 942 | 1/1990 | European Pat. Off. | |
| 0 391 179 A2 | 10/1990 | European Pat. Off. | |
| 0 394 111 | 10/1990 | European Pat. Off. | |
| WO 91/16024 | 10/1991 | WIPO | A61F 13/00 |
| WO 93/05162 | 3/1993 | WIPO | |
| WO 93/24640 | 12/1993 | WIPO | C12N 15/85 |
| WO 94/00569 | 1/1994 | WIPO | C12N 15/00 |
| WO 94/05624 | 3/1994 | WIPO | C07C 233/36 |

OTHER PUBLICATIONS

Remy et al., Chemical Abstract, vol. 121, abstract 247368, 1994.
Behr et al., Chemical Abstracts, vol. 114, abstract 24827, 1990.
Murakami et al, "Aggregate Morphology and Intermembrane Interaction of Synthetic Peptide Lipids Bearing Various Head Groups," J Am Chem Soc 107(7):2161–2167 (1985).
Murakami et al, "Preparation of Stable Single-Compartment Vesicles with Cationic and Zwitterionic Amphiphiles Involving Amino Acid Residues," J Org Chem 47(11):2137–2144 (1982).
Murakami et al, "Synthesis of Macrocyclic Enzyme Models. Part 6. Preparation and Guest-Binding Behaviour of Octopus Cyclophanes," J Chem Soc Perkin Trans I 6:1289–1299 (1988).
Murakami et al., "Synthetic Peptide Lipids Having Axial Chirality. Preparation and Aggregate Morphology.," Chemistry Letters, Tokyo JP 7:1481–1484 (1987).

Singhal et al, "Direct Gene Transfer by Liposomes," Journal Liposome Research 4(1):289–299 (1994).
Behr et al, "Efficient gene transfer into mammalian primary endocrine cells with lipopolyamine-coated DNA," Proc. Natl. Acad. Sci. USA 86:6982–6986 (1989).
Felgner et al, "Enhanced Gene Delivery and Mechanism Studies with a Novel Series of Cationic Lipid Formulations," The Journal of Biological Chemistry 269(4):2550–2561 (Jan. 23, 1994).
Gao et al, "A Novel Cationic Liposome Reagent for Efficient Transfection of Mammalian Cells", Biochemical and Biophysical Research Communications 179(1):280–285 (Aug. 30, 1991).
Nabel et al, "Direct gene transfer with DNA-liposome complexes in melanoma: Expression, biologic activity, and lack of toxicity in humans", Proc. Natl. Acad. Sci. USA 90:11307–11311 (Dec. 1993).
Nabel et al, "Gene Transfer In Vivo with DNA-Liposome Complexes: Lack of Autoimmunity and Gonadal Localization," Human Gene Therapy 3:649–656 (1992).
Zhu et al, "Systemic Gene Expression After Intravenous DNA Delivery into Adult Mice," Science 261:209–211 (Jul. 9, 1993).
Greene et al., ""Protection for the Amino Group"," Protective Groups In Organic Synthesis (2nd Ed.) (John Wiley & Sons) pp. 309–131 and 441–452 (1990).
Remy et al., "Gene Transfer with a Series of Lipophilic DNA-Binding Molecules," Bioconj Chem 5(6):647–654 (1994).
Behr, Jean-Paul, "DNA Strongly Binds to Micelles and Vesicles Containing Lipopolyamines or Lipointercalants," Tet Lett 27(48):5861–5864 (1986).
Behr, Jean-Paul, "Synthetic Gene-Transfer Vectors,"Acc Chem Res 26:274–278 (1993).
Felgner, Philip L., "Particulate systems and polymers for in vitro and in vivo delivery of polynucleotides," Advanced Drug Delivery Reviews 5:163–187 (1990).
Firestone et al., "Lysosomotropic Agents II. Synthesis and Cytotoxic Action of Lysosomotropic Detergents," Lysosomotropic Detergents pp. 1455–1464 (1979).
Firestone et al., "Lysosomotropic Agents. 1. Synthesis and Cytotoxic Action of Lysosomotropic Detergents," J Med Chem 22(9):1130–1133 (1979).

(List continued on next page.)

*Primary Examiner*—Richard L. Raymond
*Attorney, Agent, or Firm*—Daryl D. Muenchau

[57] ABSTRACT

The present invention is directed to new cationic lipids and intermediates in their synthesis that are useful for transfecting nucleic acids or peptides into prokaryotic or eukaryotic cells. The lipids comprise one or two arginine, lysine or ornithine residues linked to a lipophilic moiety. The lipids form a composition when mixed with polyanions such as nucleic acids. The compositions permit efficient transfer of polyanions into cells without significant toxicity to the cells.

20 Claims, No Drawings

OTHER PUBLICATIONS

Firestone et al., "Lysosomotropic Agents. 7. Broad–Spectrum Antifungal Activity of Lysosomotropic Detergents," J Med Chem 30:1519–1521 (1987).

Firestone et al., "Selective Delivery of Cytotoxic Compounds to Cells by the LDL Pathway," J Med Chem 27:1037–1043 (1984).

Forster et al., "The effect of lysosomotropic detergents on the permeability properties of the lysosome membrane," Biochem Biophys Acta 924:452–457 (1987).

Hussain et al., "Killing of Saccharomyces cerevisiae by the Lysosomotropic Detergent N–Dodecylimidazole," Antimicro AG & Chemo 31(4):512–517 (1987).

Legendre et al., "Delivery of Plasmid DNA into Mammalian Cell Lines Using pH–Sensitive Liposomes: Comparison with Cationic Liposomes." Pharm Res 9(10):1235–1242 (1992).

Reimer et al., "Formation of Novel Hydrophobic Complexes between Cationic Lipids and Plasmid DNA," Biochem 34:12877–12883 (1995).

Bajusz, "Contribution to the Discussion on the Protecting Groups of Arginine," Acta Chim Acad Sci Hungary 44:31 (1965).

Paulay et al., "A Novel Protection for the Guanidino Group of Argnine," Acta Chim Acad Sci Hungary 43:147–148 (1965).

Loeffler et al., "Gene Transfer into Primary and Established Mammalian Cell Lines with Lipopolyamine–Coated DNA," Methods In Enzymology, 217:599–618 (1993).

Koo et al., "A study on the hydrolysis of p–nitrophenyl carboxylates by micellar surfactants catalysts containing histidyl residue", 111(17):149399e, Chem AB, Oct. 23, 1989

Korakas et al., "Structure–retention relationships of diastereopmeric mixtures of lipidic amino acid conjugates on reversed–phase stationary phases", 659:307–315, Journal of Chromatography, 1994.

Murakami et al., "General–Base Catalysis of the Hydrolysis of p–Nitrophenyl Carboxylates by Micellar Surfactants Involving a Histidyl Residue", 103:2750–2756, J Am Chem Soc, 1981.

Murakami et al., "Catalytic Efficiency of Functionalized Vesicles in the Transamination of Pyridoxal-5'–phosphate with a Hydrophobic Amino Acid", 55:3004–3012, Bull Chem Soc Jpn, 1982.

Murakami et al., "Aggregation Behavior of Amphiphiles Functionalized with Dipeptide Segments and Enantioselective Ester Hydrolysis in Their Bilayer Membranes", 58(1):172–180, Bull Chem Soc Jpn, 1985.

Shinozuka et al., "Enantiomeric Bleomycin Model Compounds Bearing Long Alkyl–Chain", 32(47):6869–6872, Tet Lett, 1991.

CATIONIC LIPIDS

BACKGROUND OF THE INVENTION

The present invention relates to new cationic lipids and intermediates therefore as well as their use for delivering polyanionic polymers into eukaryotic and prokaryotic cells.

Lipids that are useful for transfecting nucleic acids into cells and their use have been described (WO 94/05624; WO 94/00569; WO 93/24640; WO 91/16024; WO 90/11092; U.S. Pat. Nos. 5,283,185, 5,171,687 and 5,286,634; Felgner et al *J. Biol. Sci.* (1994) 269:2550; Nabel et al *Proc. Natl. Acad. Sci. (U.S.A.)* (1993) 90:11307; Nabel et al *Hum. Gene Ther.* (1992) 3:649).

OBJECTS OF THE INVENTION

It is an object of the invention to provide cationic lipids and intermediates for making such lipids.

Another object of the invention is to provide cationic lipids that are suitable for delivering polyanionic polymers such as nucleic acids into cells in the presence of serum or blood.

Another object of the invention is to provide cationic lipids that are suitable for efficiently delivering polyanionic polymers such as nucleic acids or into cells using cells at a cell confluency of about 50% to 100%.

Another object of the invention is to provide cationic lipids that are suitable for efficiently delivering a large amount of polyanionic polymers such as nucleic acids into cells.

Another object of the invention is to provide cationic lipids having improved pharmacologic properties.

SUMMARY OF THE INVENTION

The invention is directed to new cationic lipids having the structure A, B or C

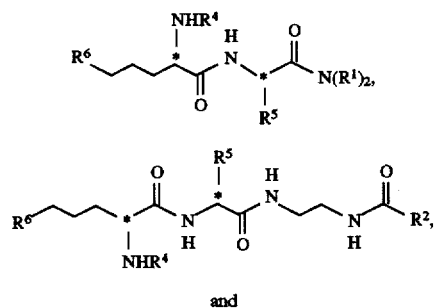

and

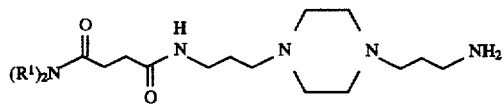

wherein $R^1$ is alkyl (12–22 C, i.e., having 12 to 22 carbon atoms) or a mono unsaturated alkenyl (12–22 C) group; $R^2$ has the structure

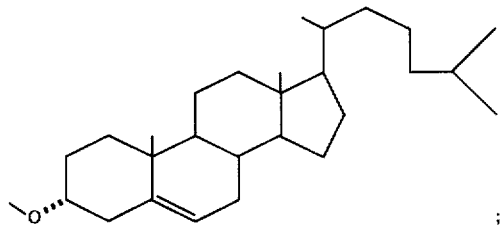

$R^4$ is hydrogen or is a protecting group; $R^5$ is H, $CH_3$, $CH(CH_3)_2$, $CH_2CH(CH_3)_2$, $CH(CH_3)CH_2CH_3$, $CH_2C_6H_5$, $CH_2C_6H_4$—p—OH, $CH_2OH$, $CH(OH)CH_3$, $(CH_2)_4NHR^4$, $(CH_2)_3NHR^4$ or $(CH_2)_3NR^4C(NH)NHR^4$; $R^6$ is $NHR^4$, $CH_2NHR^4$ or $NR^4C(NH)NHR^4$.

Other embodiments of the invention include intermediates that are useful for synthesizing the invention cationic lipids. These intermediates have the structure D or E

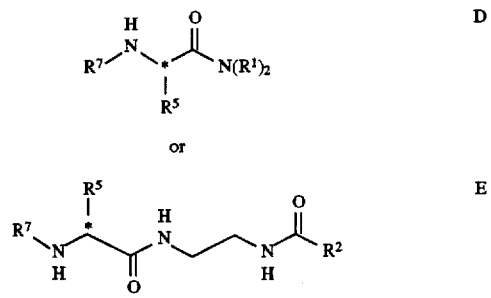

wherein $R^7$ is hydrogen or a protecting group, provided that for compounds containing both $R^4$ and $R^7$, such as D or E wherein $R^5$ consists of a group such as $(CH_2)_3NR^4C(NH)NHR^4$, $R^7$ can be removed without removing $R^4$.

Positions designated "*" are carbon atoms having substituents in the R, S or RS configuration.

DETAILED DESCRIPTION OF THE INVENTION

The invention lipids form a complex with polyanions such as nucleic acids through attraction between the positively charged lipid and the negatively charged polyanion. The complexes may comprise multilamellar or unilamellar liposomes or other particles. Hydrophobic interactions between the cationic lipids and the hydrophobic substituents in the polyanion such as aromatic and alkyl groups may also facilitate complex formation. The invention lipids efficiently deliver nucleic acids into cells in the presence of serum and thus are suitable for use in vivo or ex vivo.

The lipids and their intermediates are synthesized as shown in schemes 1 and 2 below.

SCHEME 1

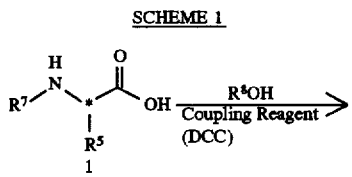

SCHEME 1 (-continued)

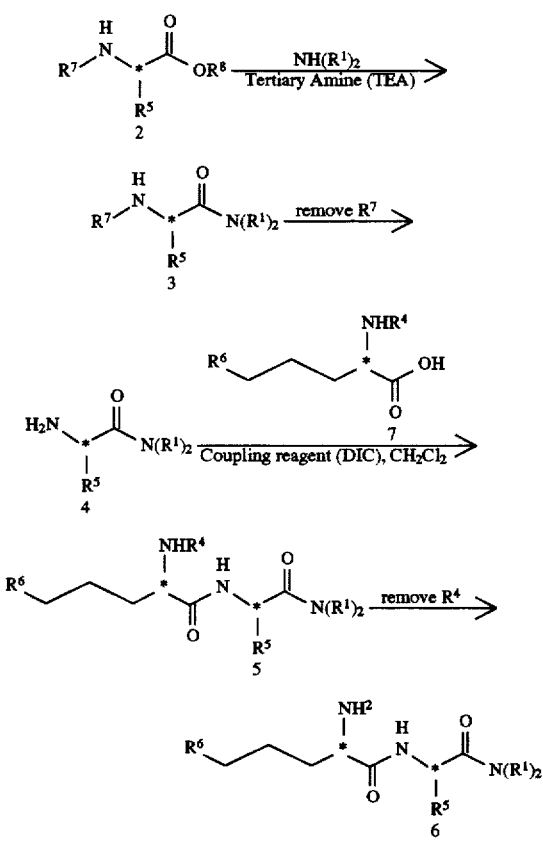

The unprotected carboxyl group shown in structure 1 of scheme 1, is activated by reacting 1, where R⁷ is a protecting group, with a suitable activating group (R⁸OH) in the presence of a coupling reagent such as dicyclohexylcarbodiimide (DCC), diisopropylcarbodiimide (DIC), N-hydroxybenzotriazolephosphoryl chloridate (BOP—Cl), isobutyl chloroformate, N,N'-carbonyldiimidazole or the like to form the activated ester group in 2 using previously described methods (see, for example, J. March, editor, *Advanced Organic Chemistry*, Wiley & Sons, third edition, 1985, p 348–351). Any amine groups at $R^5$ will also be protected with an $R^4$ protecting group. Such activating groups linked to the amino acid (—$OR^8$) function as a leaving group for synthesizing 3 or 11. Suitable $R^8OH$ activating groups include N-hydroxysuccinimide, p-nitrophenol, pentachlorophenol, pentafluorophenol and the like. The activated ester is reacted with approximately one equivalent each of a secondary amine and a tertiary amine such as ethyldiisopropyl-amine or triethylamine (TEA) to yield structure 3. The amino protecting group $R^7$ is removed to yield 4 which is coupled with a compound of structure 7 to yield 5, a protected lipid. The $R^4$ amino protecting group(s) present on the protected lipid 5 is removed to yield the free lipid.

Compounds of structure 2 shown in scheme 1 wherein $R^5$ contains an amine group(s) will also have an $R^4$ amine protecting group in synthesizing 5 so as to avoid forming adducts at the $R^5$ amino groups. In these compounds, the $R^7$ amine protecting group and the $R^4$ amine protecting group will be different so that $R^7$ can be removed without removing $R^4$, i.e., $R^7$ and $R^4$ are different and can be differentially removed from a given molecule. In general, any $R^4$ present in 7 will be the same as $R^4$ in 2.

The $R^4$ and $R^7$ amine protective groups will be selected from groups that have been described (see for example, T. W. Greene et al. editors, *Protective Groups in Organic Chemistry*, second edition, 1991, Wiley, p 309–405, p 406–412 and p 441–452). Amine protective groups such as benzyl carbamate (Cbz), p-methoxybenzyl carbamate (Moz), p-bromobenzyl carbamate, 9-fluorenylmethyl carbamate (FMOC), or 2,4-dichlorobenzyl will be used where an acid stable protective group is desired while protective groups such as t-butyl carbamate (t-BOC) or 1-adamantyl carbamate (Adoc) will be used where a base stable or nucleophile stable group is desired. Protective groups will be used to protect amine groups for where coupling reactions are carried out such as in conversion of 1 to 2 or 4 to 5. Protective groups such as 2-(2'- or 4'-pyridyl)ethyl carbamate will be used where a group stable to catalytic palladium-carbon hydrogenation or to trifluoroacetic acid is desired. The $R^4$ group can thus be selected from a diverse group of known protective groups as needed. Exemplary $R^4$-$R^7$ groups that can be present in 2 include the following pairs of protective groups. Other suitable $R^4$-$R^7$ pairs are determined experimentally by routine methods using the relative reactivity information of the different amine protective groups described by Greene et al. supra at p 406–412 and p 441–452. Acceptable exemplary $R^4$-$R^7$ pairs are shown below.

| $R^4$ | $R^z$ | $R^z$ cleavage condition |
|---|---|---|
| t-BOC | Cbz | hydrogenation |
| Cbz | t-BOC | acid hydrolysis |
| FMOC | Cbz | hydrogenation |
| Adoc | Cbz | hydrogenation |
| t-BOC | FMOC | base hydrolysis |
| FMOC | t-BOC | acid hydrolysis |

Lipids containing cholesterol are synthesized as shown in scheme 2.

SCHEME 2

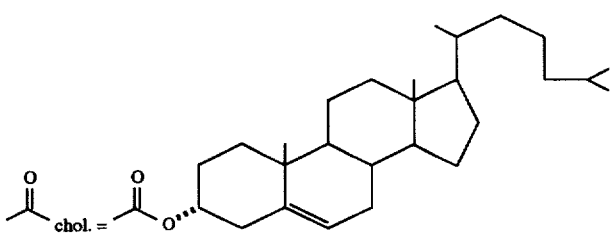

-continued
SCHEME 2

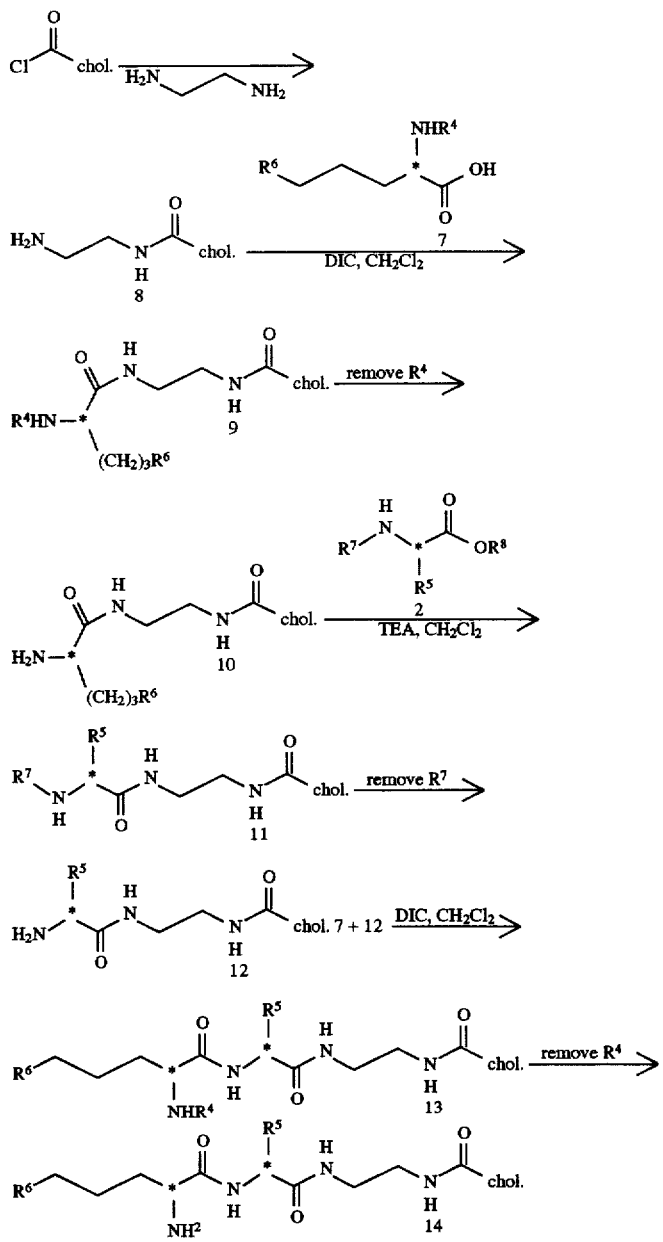

Cholesteryl chloroformate (Aldrich, Cat. No. C7,700-7) is coupled to ethylenediamine in organic solvent ($CH_2Cl_2$) at 0–24° C. to obtain 8. 8 is converted to the protected lipid intermediate 9 by reaction with 7 or is converted to 11 by reaction with 2. The protected lipid intermediates 9, 11 and 13 are deprotected as shown in scheme 2 to obtain free lipids 10 and 14 or the partially deprotected lipid (when an amine group is present at $R^5$) 12.

Lipid intermediates of structure 11 contain both $R^4$ and $R^7$ amine protective groups. As described for intermediates in scheme 1 that contain both $R^4$ and $R^7$, the protective groups will be differentially removable from the protected lipid intermediate, 11. The same pairs of differentially removable amine protective groups can be used as described. The $R^4$ group present in 7 will generally be the same as $R^4$ present in 2 which permits removing all $R^4$ from 13 using a single set of conditions.

Intermediates of structure $HN(R^1)_2$ can be synthesized by reacting an acyl chloride of structure $ClC(O)R^9$ wherein $R^9$ is alkyl (11–21 C) or mono unsaturated alkenyl (11–21 C), with $H_2NR^1$ to obtain the intermediate $HN(R^1)[C(O)R^9]$ which is reduced (using, for example, lithium aluminum hydride) to yield $HN(R^1)_2$. The acyl chlorides are obtained by reaction of the free fatty acid with, for example, oxalyl chloride, $SOCl_2$ or $PCl_3$. The $H_2NR^1$ intermediate is obtained by reacting $ClC(O)R^9$ with ammonia gas (at about 0° C. In addition, many $ClC(O)R^9$ chlorides and $H_2NR^1$ amines are available commercially (Aldrich Chemical, Kodak, K&K Chemicals).

Exemplary $R^1$ have the structures —$(CH_2)_{19}CH_3$, —$(CH_2)_{17}CH_3$, —$(CH_2)_{15}CH_3$, —$(CH_2)_{13}CH_3$, —$(CH_2)_{11}CH_3$, —$(CH_2)_5CH=CH(CH_2)_7CH_3$ and —$(CH_2)_8CH=CH(CH_2)_7CH_3$. The alkenyl species are in a cis or trans configuration at the double bond. In general, each $R^1$ on a given molecule will have the same structure, although they may be different.

Exemplary invention cationic lipids and their protected precursors have the structures

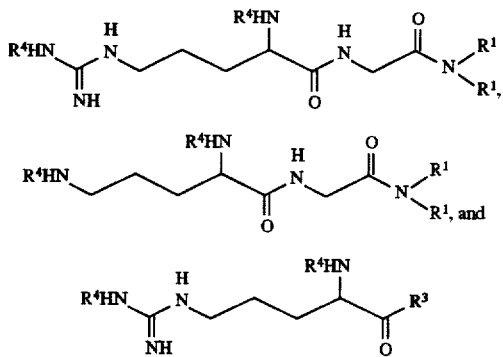

wherein $R^1$ and $R^4$ have the meanings given, and $R^3$ is a substituted cholesteryl moiety having the structure

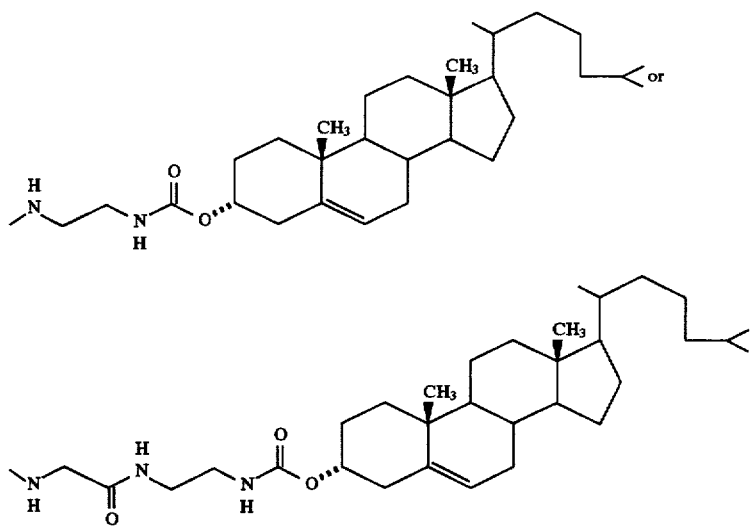

The salts include pharmaceutically or physiologically acceptable non-toxic salts of these compounds. Such salts may include those derived by combination of appropriate cations such as alkali and alkaline earth metal ions or ammonium and quaternary amino ions with the acid anion moiety of the phosphate or phosphorothioate acid group present in polynucleotides. In addition salts may be formed from acid addition of certain organic and inorganic acids with basic centers of the purine, specifically guanine, or pyrimidine base present in polynucleotides. Suitable salts of the invention cationic lipids include acid addition salts such as HCl, HBr, HF, HI, $H_2SO_4$, and trifluoroacetate. Finally it is to be understood that compounds of the present invention in their un-ionized as well as zwitterionic form and/or in the form of solvates are also considered part of the present invention.

Cationic lipid-polyanionic polymer complexes are formed by preparing lipid particles consisting of either (1) an invention cationic lipid or (2) an invention cationic lipid-colipid mixture, followed by adding a polyanionic polymer to the lipid particles at about room temperature (about 18° to 26° C). The mixture is then allowed to form a complex over a period of about 10 min to about 20 hours, with about 15 to 60 min most conveniently used. The complexes may be formed over a longer period, but additional enhancement of transfection efficiency will usually not be gained by a longer period of complexing. A phospholipid such as DOPE is generally used as a colipid with the invention lipids to enhance the efficiency of polyanion delivery into cells. Additional colipids that are suitable for preparing lipid complexes with the invention cationic lipids are dimyristoylphosphatidylethanolamine, dipalmitoylphosphatidylethanolamine, palmitoyloleoylphosphatidylethanol-amine, cholesterol, distearoylphosphatidylethanolamine, phosphatidylethanolamine covalently linked to polyethylene glycol and mixtures of these colipids.

The invention cationic lipids can be used without a colipid but are preferably used with a colipid to obtain a high transfection efficiency. The optimal cationic lipid:colipid ratio for a given invention cationic lipid is determined by mixing experiments to prepare lipid mixtures for complexing with a polyanion using cationic lipid:colipid ratios between about 1:0 and 1:10. Methods to determine optimal cationic lipid:colipid ratios have been described (see, for example, Felgner, infra). Each lipid mixture is optionally tested using more than one nucleic acid-lipid mixture having different nucleic acid:lipid molar ratios to optimize the nucleic acid:lipid ratio.

Suitable molar ratios of invention lipid:colipid are about 0.1:1 to 1:0.1, 0.2:1 to 1:0.2, 0.4:1 to 1:0.4, or 0.6:1 to 1:0.6. Lipid particle preparations containing increasing molar proportions of colipid were found to deliver increasing amounts of nucleic acid to transfected cells as the proportion of colipid increased. The amount of polyanion, present as an oligonucleotide, delivered to a representative cell by at least some of the invention lipids was found to be significantly greater than the amount delivered by commercially available transfection lipids {Lipofectin™ (Gibco/BRL), Transfectam™ (Promega) or Lipofectamine™ (Gibco/BRL)} for all cell lines where comparisons were made. The difference in transfection efficiency between invention lipids and commercially available lipids is usually most pronounced when the transfections are done in the presence of medium containing serum. The amount of polyanion delivered into cells was estimated to be about 2- to 100-fold greater for invention lipids 30, 34 and 35 based on the observed fluorescence intensity of transfected cells after transfection using a fluorescently labeled oligonucleotide. The invention cationic lipids also transfect some cell types that are not detectably transfected by commercial lipids, particularly where the transfection is conducted in the presence of serum.

The invention cationic lipids also differed from commercially available lipids by efficiently delivering a polyanion (oligonucleotide) into cells in tissue culture over a range of cell confluency from about 50 to 100%. Most commercially available lipids require cells that are at a relatively narrow confluency range for optimal transfection efficiency. For example, Lipofectin™ requires cells that are 70–80% confluent for transfecting the highest proportion of cells in a population. The invention lipids could be used to transfect cells that are about 10–50% confluent, but toxicity of the lipids was more pronounced, relative to that seen using cells that are about 50–100% confluent. In general, the invention lipids transfected cells that were about 60–100% confluent with minimal toxicity and optimal efficiency. Confluency ranges of 60–95% or 60–90% are thus convenient for transfection protocols with most cell lines in tissue culture.

The invention cationic lipids complexed with an oligonucleotide, RNA or plasmid DNA were used to transfect cells in tissue culture. Similarly, lipids complexed with plasmid DNA were used to transfect cells in mice. The RNA and the DNA encoded gene products that were expressed in the transfected cells.

Liposomes or complexes consisting of the invention cationic lipids and a colipid are conveniently prepared by first drying the lipids in solvent (usually chloroform) under reduced pressure (spin vac in 1.5 mL polypropylene tubes for small volumes (about 100 µL) or rotovap in round bottom flasks for larger volumes, e.g. 10 mL in 100 mL flask). The lipids are then hydrated and converted to liposomes or lipid complexes by adding water or low ionic strength buffer (less than about 200 mM total ion concentration) followed by agitating (by vortexing and/or sonication) and/or freeze/thaw treatments.

The invention lipid-polyanion complexes are believed to form micelles or liposomes of about 40 to 600 nm in diameter. Light scattering experiments using a 1:1 molar ratio of 34 cationic lipid and DOPE colipid (prepared by sonication as described in Example 5 below) showed two peaks corresponding to particles of about 66 nm and about 260 nm in diameter, with lesser amounts of particles above, below and between these sizes.

The invention cationic lipids 30 or 34 and DOPE colipid (1:1) were prepared by sonication and then filtered using 200, 100 or 50 nm filters to obtain particles less than about 200 nm in diameter, less than about 100 nm and less than about 50 nm. Transfection efficiency using 200 nm filtered or 100 nm filtered preparations were the most efficient (and equally efficient) with regard to both the proportion of cells transfected and the amount of nucleic acid delivered per cell. The 50 nm filtered preparations were about 40–50% as efficient as the preparations containing larger particles. The size of the particles or micelles in a given preparation will vary depending on the preparation method. Sonicating cationic lipid-colipid mixtures will provide smaller micelles and vortexing will provide larger micelles (Felgner *J. Biol. Chem.* (1994) 269:2550–2561). Such micelles are believed to transfer the polyanion into the cytoplasm of a eukaryotic or prokaryotic cell by pinocytosis, endocytosis and/or by direct fusion with the plasma membrane.

The complexes of this invention are then used to transfect one or more cell lines or administered in vivo to animals to determine the efficiency of transfection obtained with each preparation. The invention lipid-colipid complexes in medium were used at a concentration between about 0.5 and 20 µg/mL, with typical transfections using about 1.0 to 15 µg/mL of lipid. If the nucleic acid encodes a polypeptide, it also may comprise a selectable (such as neomycin phosphotransferase) or detectable (such as β-galactosidase) marker or gene that will serve to allow measuring or estimating the efficiency of transfection. Polyanions will have at least two negative charges per molecule to facilitate complex formation with the positively charged cationic lipid. Polyanions typically will have at least 5 charges per molecule or at least 10 charges per molecule. In general, oligonucleotides will have at least 2, 4, 6, 10, 14 or more charges to facilitate complex formation. However, nucleic acids containing two, three, four or more adenine residues (e.g., 4 to 10, 5 to 15 or 6 to 35 adenine residues) and no charges associated with the internucleotide linkages can be transfected with invention cationic lipids containing arginine (such as 34 or 35) because arginine and adenine form noncovalent complexes with each other.

As used herein, polynucleotide means single stranded or double stranded DNA or RNA, including for example, oligonucleotides (which as defined herein, includes DNA, RNA and oligonucleotide analogs) and plasmids. In general, relatively large nucleic acids such as plasmids or mRNAs will carry one or more genes that are to be expressed in a transfected cell, while comparatively small nucleic acids, i.e., oligonucleotides, will comprise (1) a base sequence that is complementary (via Watson Crick or Hoogsteen binding) to a DNA or RNA sequence present in the cell or (2) a base sequence that permits oligonucleotide binding to a molecule inside a cell such as a peptide, protein or glycoprotein. Exemplary RNAs include ribozymes and antisense RNA sequences that are complementary to a target RNA sequence in a cell.

Polynucleotides include single stranded unmodified DNA or RNA comprising (a) the purine or pyrimidine bases guanine, adenine, cytosine, thymine and/or uracil; (b) ribose or deoxyribose; and (c) a phosphodiester group that linkage adjacent nucleoside moieties. Polynucleotides include oligonucleotides which typically comprise 2 to about 100 or 3 to about 100 linked nucleosides. Typical oligonucleotides comprise size ranges such as 2–10, 2–15, 2–20, 2–25, 2–30, 2–50, 8–20, 8–30 or 2–100 linked nucleotides. Oligonucleotides are usually linear with uniform polarity and, when regions of inverted polarity are present, such regions comprise no more than one polarity inversion per 10 nucleotides. One inversion per 20 nucleotides is typical. Oligonucleotides can also be circular, branched or double-stranded. Antisense oligonucleotides generally will comprise a sequence of about from 8 to 30 bases or about 8 to 50 bases that is substantially complementary to a cognate DNA or RNA base sequence present in the cell. The size of nucleic acid that is delivered into a cell using the invention lipids is limited only by the size of molecules that reasonably can be prepared and thus DNA or RNA that is 0.1 to 1 Kilobase (Kb), 1 to 20 Kb, 20Kb to 40 Kb or 40Kb to 1,000Kb in length can be delivered into cells.

Polynucleotides also include DNA or RNA comprising one or more covalent modifications. Covalent modifications include (a) substitution of an oxygen atom in the phosphodiester linkage of an polynucleotide with a sulfur atom, a methyl group or the like, (b) replacement of the phosphodiester group with a nonphosphorus moiety such as —O—$CH_2$—O—, —S—$CH_2$—O—or —O—$CH_2$—S—, and (c) replacement of the phosphodiester group with a phosphate analog such as —O—P(S)(O)—O—, —O—P(S)(S)—O—, —O—P(CH₃)(O)—O— or —O—P(NHR¹⁰)(O)—O—where R¹⁰ is alkyl (C₁₋₆), or an alkyl ether (C₁₋₆). Oligonucleotides include oligomers having a substitution at about 10% to 100% or 20 to 80% of the phosphodiester groups in unmodified DNA or RNA. Oligonucleotides include covalent modification or isomers of ribose or deoxyribose such as morpholino, arabinose, 2'-fluororibose, 2'-fluoroarabinose, 2'-O-methylribose or 2'-O-allylribose. Oligonucleotides and methods to synthesize them have been described (for example see: PCT/US90/03138, PCT/US90/06128, PCT/US90/06090, PCT/US90/06110, PCT/US92/03385, PCT/US91/08811, PCT/US91/03680, PCT/US91/06855, PCT/US91/01141, PCT/US92/10115, PCT/US92/10793, PCT/US93/05110, PCT/US93/05202, PCT/US92/04294, WO86/05518, WO89/12060, WO91/08213, WO90/15065, WO91/15500, WO92/02258, WO92/20702, WO92/20822, WO92/20823, U.S. application Ser. Nos. 07/864,873, 08/123,505 and 08/050,698, U.S. Pat. No. 5,214,136 and Uhlmann Chem Rev (1990) 90:543). Typical oligonucleotides comprise size ranges such as 2–10, 2–15, 2–20, 2–25, 2–30, 2–50, 8–20, 8–30 or 2–100 linked nucleotides. Oligonucleotides are usually linear with uniform polarity and, when regions of inverted polarity are present, such regions comprise no more than one polarity inversion per 10 nucleotides. One inversion per 20 nucleotides is typical. Oligonucleotides can be circular, branched or double-stranded.

Linkage means a moiety suitable for coupling adjacent nucleomonomers and includes both phosphorus-containing moieties and non phosphorus-containing moieties such as formacetal, thioformacetal, riboacetal and the like. A linkage usually comprises 2 or 3 atoms between the 5' position of a nucleotide and the 2' or 3' position of an adjacent nucleotide.

A purine or pyrimidine base means a heterocyclic moiety suitable for incorporation into an oligonucleotide. It can be in the α or β anomer configuration. Purine or pyrimidine bases are moieties that bind to complementary nucleic acid sequences by Watson-Crick or Hoogsteen base pair rules. Bases need not always increase the binding affinity of an oligonucleotide for binding to its complementary sequence at least as compared to bases found in native DNA or RNA. However, such modified bases preferably are not incorporated into an oligomer to such an extent that the oligonucleotide is unable to bind to complementary sequences to produce a detectably stable duplex or triplex. Purine or pyrimidine bases usually pair with a complementary purine or pyrimidine base via 1, 2 or 3 hydrogen bonds. Such purine or pyrimidine bases are generally the purine, pyrimidine or related heterocycles shown in formulas 15–18.

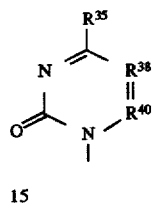

15

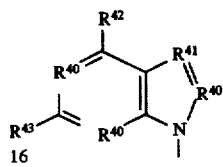

16

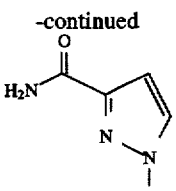

17

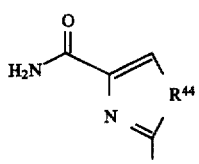

18 wherein R³⁵ is H, OH, F, Cl, Br, I, OR³⁶, SH, SR³⁶, NH₂, or NHR³⁷;

R³⁶ is C₁–C₆ alkyl (including CH₃, CH₂CH₃ and C₃H₇), CH₂CCH (2-propynyl) and CH₂CHCH₂;

R³⁷ is C₁–C₆ alkyl including CH₃, CH₂CH₃, CH₂CCH, CH₂CHCH₂, C3H7;

R³⁸ is N, CF, CCl, CBr, Cl, CR³⁹ or CSR³⁹, COR³⁹;

R³⁹ is H, C₁–C₉ alkyl, C₂–C₉ alkenyl, C₂–C₉ alkynyl or C₇–C₉ arylalkyl unsubstituted or substituted by OH, O, N, F, Cl, Br or I including CH₃, CH₂CH₃, CHCH₂, CHCHBr, CH₂CH₂Cl, CH₂CH₂F, CH₂CCH, CH₂CHCH₂, C₃H₇, CH₂OH, CH₂OCH₃, CH₂OC₂H₅, CH₂OCCH, CH₂OCH₂CHCH₂, CH₂C₃H₇, CH₂CH₂OH, CH₂CH₂OCH₃, CH₂CH₂OC₂H₅, CH₂CH₂OCCH, CH₂CH₂OCH₂CHCH₂, CH₂CH₂OC₃H₇;

R⁴⁰ is N, CBr, CI, CCl, CH, C(CH₃), C(CH₂CH₃) or C(CH₂CH₂CH₃);

R⁴¹ is N, CH, CBr, CCH₃, CCN, CCF₃, CC≡CH or CC(O)NH₂;

R⁴² is H, OH, NH₂, SH, SCH₃, SCH₂CH₃, SCH₂CCH, SCH₂CHCH₂, SC₃H₇, NH(CH₃), N(CH₃)₂, NH(CH₂CH₃), N(CH₂CH₃)₂, NH(CH₂CCH), NH(CH₂CHCH₂), NH(C₃H₇) or halogen (F, Cl, Br or I);

R⁴³ is H, OH, F, Cl, Br, I, SCH₃, SCH₂CH₃, SCH₂CCH, SCH₂CHCH₂, SC₃H₇, OR¹⁶, NH₂, or NHR³⁷; and R⁴⁴ is O, S or Se.

Exemplary bases include adenine, cytosine, guanine, hypoxanthine, inosine, thymine, uracil, xanthine, 2-aminopurine, 2,6-diaminopurine, 5-(1-butynyl)uracil, 5-(4-methylthiazol-2-yl)uracil, 5-(5-methylthiazol-2-yl)uracil, 5-(4-methylthiazol-2-yl)cytosine, 5-(5-methylthiazol-2-yl)cytosine and the like.

Also included are alkylated or alkynylated bases having substitutions at, for example, the 5 position of pyrimidines that results in a pyrimidine base other than uracil, thymine or cytosine, i.e., 5-methylcytosine, 5-(1-propynyl)cytosine, 5-(1-propynyl)uracil and the like. Base analogs and their use in oligomers have been described (see for example, U.S. application Ser. No. 08/123,505; U.S. application Ser. No. 92/10115; U.S. application Ser. No. 91/08811; U.S. application Ser. No. 92/09195; WO 93/10820; WO 92/09705; WO 92/02258; Nikiforov, T. T., et al, Tet Lett (1992) 33:2379–2382; Clivio, P., et al, Tet Lett (1992) 33:65–68; Nikiforov, T. T., et al, Tet Lett (1991) 32:2505–2508; Xu, Y.-Z., et al, Tet Lett (1991) 32:2817–2820; Clivio, P., et al, Tet Lett (1992) 33:69–72; Connolly, B. A., et al, Nucl Acids Res (1989) 17:4957–4974).

Nucleic acids complexed with the invention lipids may comprise nucleic acids encoding a therapeutic or diagnostic polypeptide. Examples of such polypeptides include histocompatibility antigens, cell adhesion molecules, cytokines, antibodies, antibody fragments, cell receptor subunits, cell receptors, intracellular enzymes and extracellular enzymes or a fragment of any of these. The nucleic acids also may optionally comprise expression control sequences and generally will comprise a transcriptional unit comprising a transcriptional promoter, an enhancer, a transcriptional terminator, an operator or other expression control sequences.

Nucleopolymers (i.e., nucleic acids, oligonucleotides or oligonucleotide analogs) used to form complexes for transfecting a cell may be present as more than one expression vector or more than one oligonucleotide. Thus, 1, 2, 3 or more different expression vectors and/or oligonucleotides are delivered into a cell as desired. Expression vectors will typically express 1, 2 or 3 genes when transfected into a cell, although many genes may be present such as when a herpes virus vector or a yeast artificial chromosome is delivered into a cell. The ratio of each nucleopolymer in a lipid complex relative to each other can be selected as desired. Expression vectors that are introduced into a cell can encode selectable markers (*E coli* neomycin phosphotransferase, thymidine kinase from a herpesvirus, *E coli* xanthine-guanine phosphoribosyl-transferase, and the like) or biologically active proteins such as metabolic enzymes (such as immunoglobulin genes, cell receptor genes, genes that encode enzymes that mediate purine or pyrimidine metabolism and the like).

Methods to prepare lipid-nucleic acid complexes and methods to introduce the complexes into cells in vitro and in vivo have been described (see for example, U.S. Pat. Nos. 5, 283,185; 5,171,678; WO 94/00569; WO 93/24640; WO 91/16024; Felgner *J Biol Chem* (1994) 269:2550; Nabel *Proc Natl Acad Sci* (*USA*) (1993) 90:11307; Nabel *Human Gene Ther* (1992) 3:649; Gershon *Biochem* (1993) 32:7143; Strauss *EMBO J* (1992) 11:417).

APPLICATIONS

The invention lipids are useful for delivering polyanions or nucleopolymers into cells. The invention lipids can be used to deliver an expression vector into a cell for manufacturing or therapeutic use. The vector-transformed cell can be used to produce commercially useful cell lines, such as a cell line for producing therapeutic proteins or enzymes (erythropoietin, and the like), growth factors (human growth hormone, and the like) or other proteins. The invention lipid-nucleic acid complexes can be used to construct cell lines for gene therapy applications in subjects such as humans or other species including murine, feline, bovine, equine, ovine or non human primate species. The invention lipids can be used in the presence of serum and will thus deliver polyanions into cells in tissue culture medium containing serum in vitro or in an animal in vivo.

The invention lipids complexed with nucleopolymers can be used in antisense inhibition of gene expression in a cell by delivering an antisense oligonucleotide into the cell (see for example, Wagner *Science* (1993) 260:1510; WO 93/10820). Such oligonucleotides will generally comprise a base sequence that is complementary to a target RNA sequence that is expressed by the cell. However, the oligomer may regulate intracellular gene expression by binding to an intracellular nucleic acid binding protein (Clusel *Nucl Acids Res* (1993) 21:3405) or by binding to an intracellular protein or organelle that is not known to bind to nucleic acids (WO 92/14843). A cell that is blocked for expression of a specific gene(s) is useful for manufacturing and therapeutic applications. Exemplary manufacturing uses include inhibiting protease synthesis in a cell to increase production (i.e., reduce target protein degradation caused by the protease) of a protein for a therapeutic or diagnostic application. Exemplary therapeutic applications include inhibiting synthesis of cell surface antigens (histocompatibility antigens and the like) to reduce rejection and/or to induce immunologic tolerance of the cell after it is implanted into a subject.

All citations are incorporated herein by reference.

The following examples illustrate but do not limit the invention.

EXAMPLE 1

A. Compound 19

Carbobenzyloxyglycine (1.05 g, 5 mmole) in THF (30 mL), N-hydroxysuccinimide (0.58 g, 5 mmole) and DCC (1.1 g, 5.3 mmole) were stirred at room temperature overnight. The precipitate was filtered off, washed with methylene chloride. The combined organic solution was concentrated to dryness, yielding compound 19 and used for the next reaction without further purification.

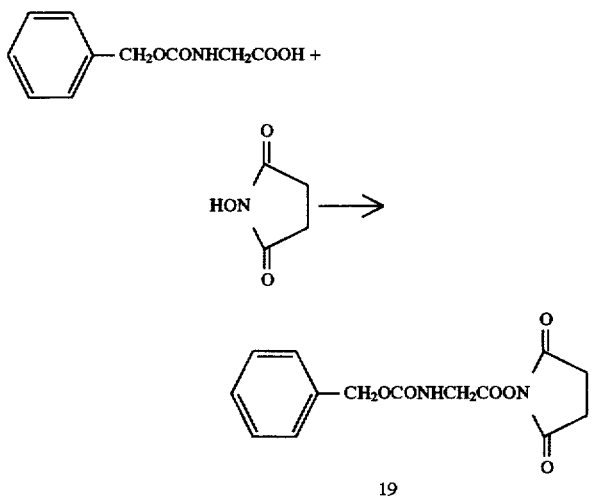

B. Compounds 20-22

Compound 20: Compound 19 was dissolved in methylene chloride (30 mL) containing TEA (1 mL), following by addition of distearylamine (2.6 g, 5 mmole). After 5 hr at room temperature, the reaction mixture was washed with water, dried over $Na_2SO_4$, concentrated. The residue was purified by flash column chromatography on silica gel, eluted with methylene chloride to afford the desired product, 20, as a colorless liquid 1.60 g; yield 45% (2 steps). NMR ($CDCl_3$): δ7.20-7.40 (m, 5 H), 5.85 (b, 1H); 5.12 (s, 2H), 4.00 (d, 2 H), 3.15 (t, 2H), 3.31 (t, 2H), 1.42-1.60 (m, 4H), 1.10-1.40 (m, 60H), 0.88 (t, 6H).

Compound 21: yield 57% (2 steps). NMR ($CDCl_3$): δ7.20-7.40 (m, 5 H), 5.85 (t, 1H); 5.12 (b, 2H), 4.00 (d, 2 H), 3.31 (t, 2H), 3.14 (t, 2H), 1.40-1.60 (m, 4H), 1.20-1.40 (m, 36H), 0.88 (t, 6H).

Compound 22. NMR ($CDCl_3$): δ7.20-7.40 (m, 5 H), 5.82 (b, 1H); 5.12 (b, 2H), 4.00 (d, 2 H), 3.31 (t, 2H), 3.14 (t, 2H), 1.40-1.60 (m, 4H), 1.10-1.40 (m, 44H), 0.88 (t, 6H).

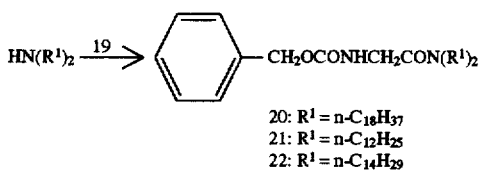

20: $R^1 = n\text{-}C_{18}H_{37}$
21: $R^1 = n\text{-}C_{12}H_{25}$
22: $R^1 = n\text{-}C_{14}H_{29}$

C. Compounds 23–25

Compound 23: Compound 20 (1.60 g, 2.24 mmole) in methylene chloride (7 mL), and ethanol (14 mL) was hydrogenated at 50 psi in the presence of 10% Pd/C for 8 hr. The catalyst was filtered off through a Celite pad. The filtrate was concentrated to afford a yellowish wax-like solid (1.27 g), 23. NMR (CDCl$_3$): δ3.51 (S, 2H), 3.48 (b, 2H); 3.30 (t, 2H), 3.15 (t, 2H), 1.45–1.51 (m, 4H), 1.10–1.40 (m, 60H), 0.88 (t, 6H).

Compound 24: yield 93%. NMR (CDCl$_3$): δ8.60 (b, 2H), 3.94 (S, 2H); 3.30 (t, 2H), 3.10–3.20 (m, 2H), 1.40–1.60 (m, 4H), 1.10–1.40 (m, 36H), 0.88 (t, 6H).

Compound 25: yield 94%. NMR (CDCl$_3$): δ8.50 (b, 2H), 4.95 (b, 2H); 3.28 (b, 2H), 3.14 (b, 2H), 1.40–1.60 (m, 4H), 1.10–1.40 (m, 44H), 0.85 (t, 6H).

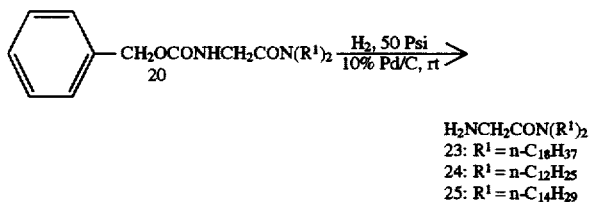

23: $R^1 = n\text{-}C_{18}H_{37}$
24: $R^1 = n\text{-}C_{12}H_{25}$
25: $R^1 = n\text{-}C_{14}H_{29}$

D. Compound 26 (t-BOC-Ornithine)

L-Ornithine.HCl (0.84 g, 5 mmole) was dissolved in H$_2$O (15 mL) containing NaOH (0.6 g, 15 mmole), followed by addition of a THF (15 mL) solution of (t-BOC)$_2$O (2.18 g, 10 mmole). The resulting mixture was stirred at room temperature overnight, then was neutralized with 1N HCl aqueous solution (pH 4), extracted with CH$_2$Cl$_2$ (50 mL) three times. The combined organic phase was dried over Na$_2$SO$_4$, concentrated, affording the title compound 26, 1.00 g, 60%.

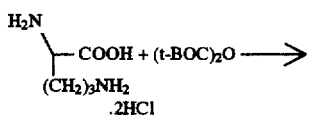

E. Compounds 27–28

Compound 27: Compound 26 (0.11 g, 0.33 mmole), 23 (0.192 g, 0.33 mmole) and DIC (46 mg, 0.36 mmole) were dissolved in CH$_2$Cl$_2$ (10 mL). After being stirred 16 hr at room temperature, the reaction was washed with water, dried, and concentrated. The residue was purified by flash column chromatography on silica gel, eluted with 3% CH$_3$OH in CH$_2$Cl$_2$ (product came off column at frs 4–11, 8 mL/fr), affording 0.2 g (69%) of product 27. MNR (CDCl1$_3$): δ7.04 (b, 1H), 5.10 (m, 1H), 4.65 (b, 1H), 4.22 (b, 1H), 4.02 (d, 2H), 3.30 (t, 2H), 3.10–3.25 (m, 4H), 1.10–1.60 (m, 86H), 0.88 (t, 6H).

Compound 28 was prepared from compounds 26 and 24 in the same manner in a 26% yield. NMR (CDCl$_3$): δ7.05 (b, 1H), 5.06 (b, 1H), 4.62 (b, 1H), 4.20 (b, 1H), 4.02 (d, 2H), 3.34 (t, 2H), 3.10–3.20 (m, 4H), 1.20–1.60 (m, 62H), 0.88 (t, 6H).

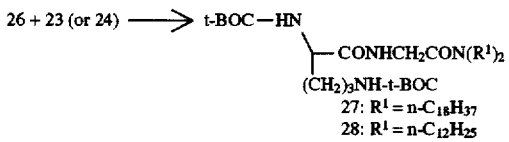

27: $R^1 = n\text{-}C_{18}H_{37}$
28: $R^1 = n\text{-}C_{12}H_{25}$

F. Compound 29. (trifluoroacetic acid salt, TFA)

Compound 27 (0.2 g) was treated with trifluoroacetic acid (exc) at room temperature for 20 min. The reaction mixture was evaporated to dryness affording a wax-like off white solid, 0.19 g. NMR (DMSO-d$_6$): δ8.58 (t, 1H), 8.18 (b, 2H), 7.75 (b, 2H), 3.95 (d, 2H), 3.90 (m, 1H), 3.10–3.25 (m, 4H), 2.70–2.82 (m, 2H), 1.10–1.60 (m, 68H), 0.88 (t, 6H).

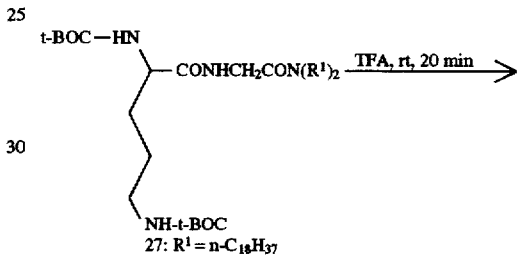

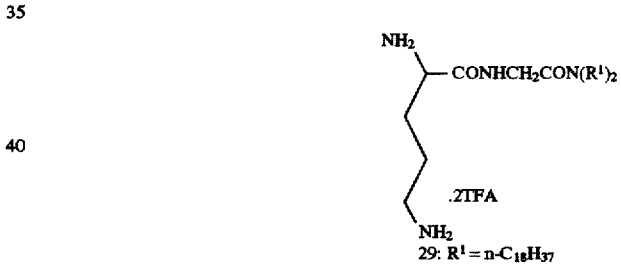

29: $R^1 = n\text{-}C_{18}H_{37}$

G. Compound 30 (HCl salt; $R^1$=n-$C_{18}H_{37}$).

Compound 27 (1.63 g; 1.82 mmole) was dissolved in 1,4-dioxane 5 mL and treated with 4N HCl in 1,4-dioxane (5 mL). After 1.5 hr at room temperature, the reaction mixture was concentrated and azeotroped with CH$_3$CN (5 times). The product weighed 1.30 g.

H. Compound 31 (HCl salt)

Compound 31 (HCl salt), was prepared from compound 28 in the same manner as compound 30.

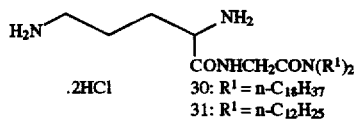

30: $R^1 = n\text{-}C_{18}H_{37}$
31: $R^1 = n\text{-}C_{12}H_{25}$

EXAMPLE 2

A-1. Compound 32

L-t-BOC-Arg (t-BOC)$_2$—OH, L-Arginine protected with t-BOC group, was purchased from BACHEM Bioscience Inc., Cat. No. A2935 (0.50 g; 1.05 mmole), compound 23 (0.58 g; 1 mmole), DIC (0.145 g; 1.15 mmole) were dissolved in $CH_2Cl_2$ (30 mL). The reaction mixture was stirred at room temperature overnight, washed with $H_2O$, dried over $Na_2SO_4$, concentrated, and purified by flash column chromatography on silica gel, affording 0.74 g of product 32 in 72% yield. NMR ($CDCl_3$): δ9.20–9.50 (m, 2H), 7.20 (b, 1H), 5.50 (d, 1H), 4.23 (m, 1H), 4.02 (m, 2H), 3.90 (t, 2H), 3.35 (m, 2H), 3.19 (t, 2H) 1.10–1.70 (m, 95H), 0.88 (t, 6H).

A-2. Compound 33

Compound 33: yield 37.5%. NMR ($CDCl_3$): δ9.15–9.50 (b, 2H), 7.20 (b, 1H), 5.20 (d, 1H), 4.23 (b, 1H), 4.02 (dd, 2H), 3.89 (t, 2H), 3.26–3.31 (m, 2H), 3.14 (t, 2H), 1.60–1.70 (m, 4H), 1.10–1.60 (m, 75H), 0.88 (t, 6H).

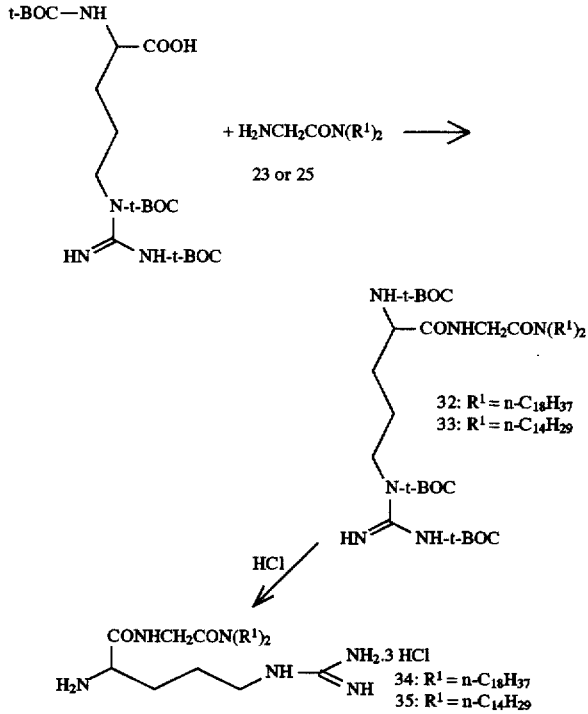

B-1. Compound 34 (HCl salt)

Compound 32 (0.6 g; 0.58 mmole) was dissolved in dioxane (4 mL) and treated with 4N HCl in dioxane (4 mL) at room temperature for 1.5 hr. The reaction mixture was concentrated, azeo-troped with $CH_3CN$ twice to yield 34. NMR (DMSO-$Cl_6$): δ9.15–9.50 (m, 2H), 8.25 (6.4H), 3.80–4.05 (m, 1H), 3.15–3.30 (m, 4H), 1.10–1.70 (m, 68H), 0.88 (t, 6H).

B-2. Compound 35 (HCl salt)

Compound 35 was synthesized in the same manner as 34 using 33 as a starting material. NMR ($CDCl_3$): δ4.10 (b, 1H), 3.78 (m, 2H), 3.65 (m, 2H), 3.20–3.35 (b, 4H), 1.10–1.70 (m, 52H), 0.88 (t, 6H).

EXAMPLE 3

A. Compound 36

A pyridine solution (20 mL) of disterylamine (2.62 g; 5 mmole) and succinic anhydride (1.5 g; 15 mmole) was stirred at room temperature for 30 hr. The reaction mixture was concentrated to dryness. The residue was partitioned between $CH_2Cl_2$ and 1M TEAB (triethylammonium bicarbonate) aqueous solution. The organic phase was isolated, dried, concentrated to afford a yellowish wax-like of product, 3.38 g, 98% yield. NMR ($CDCl_3$): δ3.20–3.340 (2t, 4H), 2.65 (s, 4H), 1.40–1.60 (m, 4H), 1.20–1.40 (m, 60H), 0.88 (t, 6H).

B. Compound 37

To a THF solution (10 mL) of compound 36 (0.62 g; 1 mmole), N-hydroxysuccinimide (0.13 g; 1.1 mmole) and DMAP (20 mg) was added DIC (0.14 g; 1.1 mmole). The resulting solution was stirred at room temperature overnight. The reaction mixture was concentrated. The residue was then partitioned between $CH_2Cl_2$ and water. The organic phase was isolated, dried, concentrated to give a wax-like product, 37 0.79 g (97%).

C. Compound 38

A methylene chloride solution (10 mL) of compound 37 (0.29 g; 0.27 mmole) and 1,4-Bis(3-amino-propyl) piperazine (1.12g; 5.6 mmole) was stirred at room temperature overnight. The reaction mixture was washed twice with water, dried, concentrated to give 0.19 g of product, 38 86% yield. NMR ($CDCl_3$): δ7.15 (t, 1H), 3.29–3.35 (m, 6H), 2.75 (t, 4H), 2.65 (t, 2H), 2.32–2.58 (m, 14H), 1.20–1.80 (m, 68H), 0.88 (t, 6H).

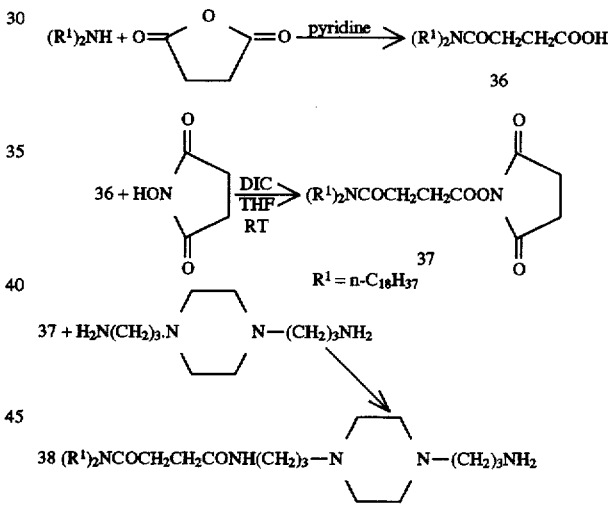

EXAMPLE 4

Compound 39

To $CH_2Cl_2$ (20 mL) about 0° C. solution of ethylenediamine (2.170 g; 44.5 mmole) was added dropwise a $CH_2Cl_2$ solution (20 mL) of cholesteryl chloroformate (1.0 g; 2.2 mmole). After being stirred at room temperature for 1 hr, the reaction was washed with $H_2O$, saturated $NaHCO_3$ aqueous solution, dried and concentrated to give a white solid (1.03 g). NMR ($CDCl_3$): δ5.37 (d, 1H), 4.93 (m, 1H), 4.54 (m, 1H), 3.21 (q 2H), 2.81 (t, 2H), 2.20–2.45 (m, 2H).

Compound 40

A $CH_2Cl_2$ (10 mL) solution of L-t-BOC-Arg(t-BOC)$_2$—OH (0.2 g; 0.42 mmole), compound 39 (0.2 g; 0.42 mmole) and DIC (58 mg; 0.46 mmole) was stirred at room temperature for 4 hrs. The reaction was worked-up as compound 32 and purified by flash column chromatography affording 0.31 g, 79%, of white powder product compound 40. NMR (CDCl$_3$): δ9.30–9.45 (m, 2H), 7.20 (b, 1H), 5.90–6.0 (m, 1H), 5.38 (m, 2H), 4.30–4.55 (b, 2H), 4.00 (m, 2H), 3.20–3.45 (m, 4H).

Compound 41

Compound 41 was synthesized from compounds 26 and 39 in 52% yield. NMR (CDCl$_3$): δ6.85 (b, 1H), 5.38 (d, 1H), 5.15–5.25 (m, 2H), 4.70–4.80 (b, 1H), 4.40–4.55 (m, 1H), 4.20 (b, 1H), 4.00 (m, 1H), 3.00–3.40 (m, 6H).

Compound 42

Compound 42 was prepared from compound 40 in the same manner as compound 30.

Compound 43

Compound 43 was prepared by treating compound 41 with 2N HCl in dioxane.

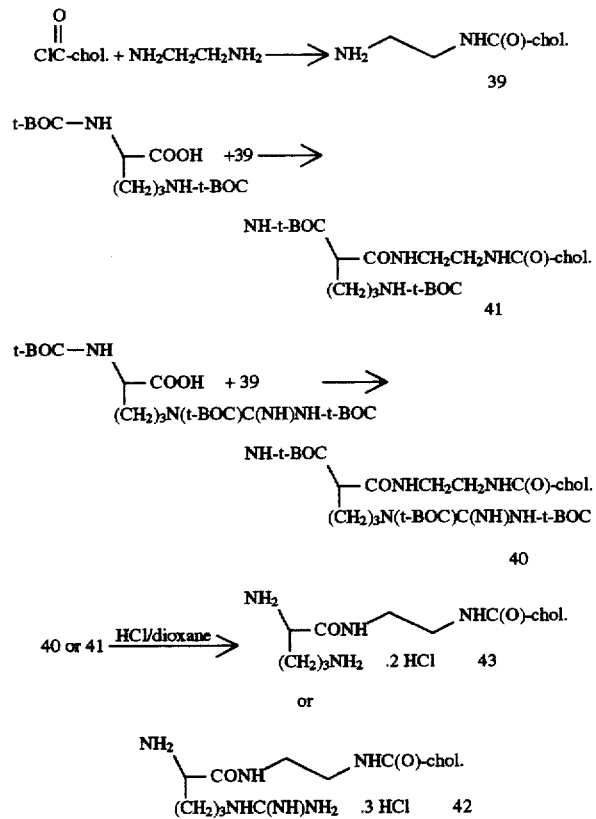

EXAMPLE 5

Preparation of lipid-nucleic acid complexes and cell transfection. Lipids were prepared for complexing with nucleic acids by drying a cationic lipid-colipid mixture in CHCl$_3$ under argon. The molar ratio of cationic lipid to colipid was adjusted by adding appropriate amounts of each lipid in CHCl$_3$ together prior to drying. Usually 10 mL of water was added to a 100 mL round bottom flask containing a dried film of lipid and colipid. The lipids consisted of a mixture of an invention cationic lipid and the colipid DOPE (dioleylphosphatidylethanolamine). Sterile-filtered water or a low ionic strength aqueous buffer such as physiological saline, TE (10 mM tris, 1 mM EDTA, pH 7–8) or Ringer's solution was then added to the dried lipids to obtain a lipid suspension at 1 mg lipid/mL followed by a 10 minute bath sonication (Ultra Sonik 100, NEY) at room temperature to suspend the lipids in the flask. The suspended lipids (10 mL) were then sonicated 5 times for 15 seconds per sonication at 0°–4° C. with about 30–60 seconds between pulses. Sonication was usually conducted in a 15 mL polypropylene culture tube. A probe sonicator (Sonifier 250, Branson Ultrasonics) was used at maximum power for the ice bath sonication and for each 15 second pulse. The lipid suspension was optionally filtered or centrifuged (2000 rpm, 10 minutes at 0°–4° C.) to remove large particulate matter and the resulting lipid suspensions were kept at 4° C. until used.

Lipid nucleic acid complexes were prepared by mixing (a) 10% v/v (usually 100 µL) oligonucleotide in Optimem™ (Bethesda Research Labs, Inc.) at room temperature (about 19°–24° C.) with (b) 10% v/v lipid suspension in Optimem™ at room temperature and allowing the mixture to stand for about 15 minutes, followed by adding (c) 80% v/v Optimem™ without serum or 80% v/v tissue culture medium (Modified Essential Medium (MEM), Dulbecco's Modified Eagle's Medium (DMEM), etc.) containing 0–80% fetal bovine serum (Hyclone, Inc.). The lipid and nucleic acid solutions could also be prepared using DMEM without serum, a low ionic strength (less than about 200 mM total ion concentration) aqueous medium lacking phosphate (TE, etc) or water in place of Optimem™. Typically, 100 µL each of Optimem™ containing oligonucleotide (100–500 pmole) and Optimem™ containing added lipid was mixed with 800 µL of serum free Optimem™ or with 800 µL of tissue culture medium containing 10–80% FBS. Generally, 5 or 10 µL (5 or 10 µg) of lipid was added to 95 or 90 µL of Optimem™ to give a final 1 mL transfection preparation containing 5 or 10 µg of lipid and 250 pmole of oligonucleotide. The lipid-nucleic acid mixture was held at room temperature for about 15 min hours before adding medium to give the final transfection preparation volume (usually 1 mL) and warming to 37° C. and immediately applying onto the cells. The transfection mixture was left on the cells for 2 to 24 hours (at 37° C.), with a 6 hour time period commonly used.

Cells were typically transfected using 1 mL of transfection mixture per well in a 6-well plate. Cells at about 50–100% confluency were used. The efficiency of transfection was relatively uniform over this confluency range for the invention cationic lipids. Typical transfections with the invention lipids used cells at about 60–100% confluency. Other cationic lipids (Lipofectin™, Transfectam™ or Lipofectamine™) were used according to manufacturers instructions and cells were thus at recommended confluency for transfection with these lipids. Cells at a lower confluency (at least about 10% confluent) could usually be transfected with oligonucleotides using the invention cationic lipids, but more cell toxicity was observed relative to cells at 50–100% confluency. The increased toxicity is believed to be due, at least in part, to the high level of oligonucleotide that was delivered into the cells.

Nucleic acid typically used was a 15-mer phosphorothioate oligonucleotides that were labeled with fluorescein at the 5' or 3' terminus using a linker of structure NH$_2$(CH$_2$)$_6$—O—P(O)(OH)—O— 5' linked to the oligonucleotide at the 5' or 3' hydroxyl group. The oligonucleotide designated ODN1 was labeled at the 5' terminus and had a base sequence complementary to a region of the HSV strain 17 DNA polymerase gene at coordinates 421 to 436 (McGeoch

*J Gen Virol* (1988) 69:1531). There was no known sequence that was complementary to ODN1 or ODN2 in the tested cells, except where ODN2 without the fluorescent label (ODN2A) was used to inhibit T antigen synthesis in an antisense assay. The oligonucleotide designated ODN2 was labeled at the 3' terminus and consisted of the same bases and the same base sequence as the oligonucleotide designated TAg-15 (Wagner *Science* (1993) 260:1510–1513, at page 1511, Table 1). The oligonucleotides were used at a concentration of 250 or 500 nM (i.e., 250 to 500 pmole) for typical 1 mL transfections.

Cells for transfection experiments were generally seeded onto 25 mm diameter glass cover slips in 6-well plates 12–24 hours prior to transfection and were grown under conditions recommended for each cell line. The cells were generally grown on cover slips to facilitate analysis by fluorescence microscopy. The cells were washed twice with tissue culture medium containing serum or with serum-free Optimem™, followed by adding 1 mL of the lipid-nucleic acid mixture at room temperature. The cells were incubated with the lipid-nucleic acid mixture at 37° C. for 2 to 24 hours, followed by washing the cells twice in medium containing serum. The cell washes were done by removing most of the medium from the wells, but leaving a thin layer, and adding about 1 mL of fresh medium for each wash. Removing all medium from the cells between each wash resulted in increased cell toxicity relative to washes with a thin layer of medium present at all times. Transfection efficiency and lipid toxicity was examined by fluorescence microscopy essentially as described (Wagner et al *Science* (1993) 260:1510) shortly after the lipid-nucleic acid complex was removed.

Transfected cell lines were A10 (rat smooth muscle, ATCC No. CRL 1476), CV-1 (African green monkey kidney, ATCC No. CCL 70), NIH 3T3 (murine fibroblast), HeLa (human cervical carcinoma, ATCC No. CCL 2), SK-OV-3 (human ovary carcinoma, ATCC No. HTB 77), HL60 (human lymphoma, ATCC No. CCL 240), HUVEC (human primary umbilical endothelial cells), ECL (human endothelial cells, ATCC No. CRL 1730), NHEK (normal human epidermal keratinocyte, Clonetics™ No. CC-2603), L7 (murine connective tissue cells), Caov-3 (human ovary carcinoma, ATCC No. HTB 75), SK-BR-3 (human breast adenocarcinoma, ATCC No. HTB 30), Rat-2 (rat fibroblast, ATCC CRL 1764), MCF7 (human breast adenocarcinoma, ATCC No. HTB 22) and Caco-2 (human colon adenocarcinoma cells, ATCC No. HTB 37). HUVEC cells did not tolerate exposure to PBS and were washed in medium containing serum (DMEM with 10% FBS) prior to adding lipid-nucleic acid mixture. NHEK cells were grown in KGM™ medium (Clonetics™ No. CC-3001) according to supplier's instructions. L7 cells, derived from clone 929 (ATCC No. CCL 1), were stably transfected with a dexamethasone responsive P-galactosidase gene and were grown in EMEM with 10% horse serum and nonessential amino acids or in DMEM with 10% fetal bovine serum.

EXAMPLE 6

A10 and CV-1 cells were transfected for 18 hours in medium containing 10% FBS (fetal bovine serum) using 1 mL of lipid complexed with 250 pmole ODN1 for 15 minutes prior to addition to the cells on cover slips in 6-well plates. The cells were observed by fluorescence microscopy immediately after the lipid-ODN1 complex was removed to determine the proportion of cells that were transfected as shown by nuclear staining by the fluorescent labeled oligonucleotide ODN1. The results showed that both 30 and 38 efficiently transfected both A10 and CV-1 cell lines in the presence of serum with little or no toxicity to the cells.

|  | % cells transfected | | |
|---|---|---|---|
| Compound | A10 | CV-1 | CV-1 toxicity |
| Lipofectin™* | 90 | 84 | +** |
| 30 | 95 | 85 | + |
| 38 | 85 | 70 | − |
| 44*** | <10 | <5 | − |

*N-[1-(2,3-dioleyloxy)propyl]-N,N,N-trimethyl ammonium bromide-DOPE mixture; all lipids were used at 15 µg/mL; all lipids were used as a 1:1 molar mixture with DOPE as the colipid
**(+) low toxicity with no dead cells apparent and occasional change in cell morphology; (++) significant toxicity with >40% of cells dead or dying; (−) no significant toxicity observed
***compound having structure C except that one $R^1$ was hydrogen and the other $R^1$ was n-$C_{12}H_{25}$.

EXAMPLE 7

SK-OV-3 cells were transfected for 18 hours in medium containing either 40% or 80% FBS using 1 mL of lipid complexed with 500 pmole ODN1 for 15 minutes prior to addition to the cells on cover slips in 6-well plates. The cells were observed by fluorescence microscopy immediately after the lipid-ODN1 complex was removed to determine the proportion of cells that were transfected as shown by nuclear staining by the fluorescent labeled oligonucleotide ODN1. The results showed that 30 efficiently transfected SK-OV-3 cells in the presence of serum. 80% serum approximates the serum protein and ion conditions that exist in vivo in mammalian circulation. 30 is thus suitable for transfecting cells under physiological conditions.

| lipid | % SK-OV-3 transfected | % serum |
|---|---|---|
| Lipofectin™ | 15–20 | 40 |
| 30 | 76 | 40 |
| 38 | <10 | 40 |
| Lipofectin™ | 0 | 80 |
| 30 | 72 | 80 |
| 38 | 0 | 80 |

* all lipids were used as a 1:1 molar mixture with DOPE as colipid

EXAMPLE 8

CV-1 cells were transfected for 18 hours and HL60 cells were transfected for 5 hours in medium containing different amounts of FBS using a transfection preparation consisting of 1 mL of 30 complexed with 500 pmole ODN1 for 15 minutes prior to addition to the cells on cover slips in 6-well plates. The cells were observed by fluorescence microscopy 5 hours after the lipid-ODN1 complex was removed to determine the proportion of cells that were transfected as shown by nuclear staining by the fluorescent labeled oligonucleotide ODN1. The results showed that 30 efficiently transfected the cells in the presence of reduced levels of lipid. The toxicity noted for HL60 cells may have been at least partly due to the high level of ODN1 that was delivered to the cells.

| μg/mL 30 | % CV-1 transfected | % HL60 transfected | % serum |
|---|---|---|---|
| 2.5 | 90 | —* | 10 |
| 5 | >95 | — | 10 |
| 10 | >95 | — | 10 |
| 15 | >95 | — | 10 |
| 20 | 95 | — | 50 |
| 20 | 90 | — | 80 |
| 20 | — | 76** | 10 |
| 20 | — | 77 | 0 |

*(—) transfection not done
**significant toxicity noted

EXAMPLE 9

HUVEC cells were transfected for 5 hours in medium containing different amounts of FBS using 1 mL transfection preparations consisting of of 30 (1:1 mixture with DOPE) or Lipofectin™ complexed with 500 pmole ODN1 for 15 minutes prior to addition to the cells on cover slips in 6-well plates. The cells were observed by fluorescence microscopy to determine the proportion of cells that were transfected as shown by nuclear staining. The results showed that 30 transfected HUVEC cells at a modest efficiency.

| μg/mL lipid | % HUVEC transfected | lipid | % serum |
|---|---|---|---|
| 5 | 1 | Lipofectin™ | 0 |
| 10 | 1 | Lipofectin™ | 10 |
| 5 | 1 | 30 | 10 |
| 10 | 5 | 30 | 10 |
| 15 | 5–10 | 30 | 10 |

EXAMPLE 10

EC1 cells were transfected for 5 or 6 hours and NHEK cells were transfected for 24 hours in DMEM containing 10% FBS or serum free Optimem™ using 1 mL of 30 complexed with 250 pmole ODN1 or Lipofectin™ complexed with 250 pmole ODN1 for 15 minutes prior to addition to the cells on cover slips in 6-well plates. The cells were observed by fluorescence microscopy after the lipid-ODN1 complex was removed to determine the proportion of cells that were transfected as shown by nuclear staining. The results showed that 30 efficiently transfected EC1 and NHEK cells. Fluorescence observations indicated that high levels of ODN1 were delivered into both EC1 and NHEK cells with little to moderate toxicity.

| μg/mL lipid | % EC1 transfected | % NHEK transfected | lipid | medium |
|---|---|---|---|---|
| 10 | 56* | — | Lipofectin™ | Optimem™ |
| 5 | 30* | — | 30 | DMEM |
| 10 | 43* | — | 30 | DMEM |
| 20 | 20* | — | 30 | DMEM |
| 0 | — | 0 | none | DMEM |
| 5 | — | 80–90 | 30 | DMEM |
| 10 | — | 70 | 30 | DMEM |
| 20 | — | 60 | 30 | DMEM |
| 2.5 | <5 | — | LA** | Optimem™ |
| 5 | <5 | — | LA | Optimem™ |
| 10 | 5 | — | LA | Optimem™ |
| 15 | 0 | — | LA | Optimem™ |
| 2.5 | 10*** | — | 30 | DMEM |
| 5 | 25–30*** | — | 30 | DMEM |

| μg/mL lipid | % EC1 transfected | % NHEK transfected | lipid | medium |
|---|---|---|---|---|
| 10 | 51*** | — | 30 | DMEM |
| 15 | 70*** | — | 30 | DMEM |
| 1 | — | 25 | 30 | DMEM |
| 2.5 | — | 50 | 30 | DMEM |
| 5 | — | 60–70 | 30 | DMEM |
| 10 | — | 60–70 | 30 | DMEM |

*6 hour transfection
**Lipofectamine ™ (Gibco/BRL; 2,3-dioleyloxy-N-[2(sperminecarboxamido)-ethyl]-N,N-dimethyl-1-propaminium trifluoroacetate)
***5 hour transfection

EXAMPLE 11

L7 cells were transfected for 18 hours in medium containing 20% FBS using 1 mL of 30 or Lipofectin™ complexed with 250 pmole ODN1 for 15 minutes prior to addition to the cells on cover slips in 6-well plates. The cells were observed by fluorescence microscopy after the lipid-ODN1 complex was removed to determine the proportion of cells that were transfected as shown by nuclear staining. The results showed that 30 efficiently transfected L7 cells with little or no toxicity.

| μg/mL lipid | % L7 transfected | lipid |
|---|---|---|
| 2.5 | 10 | 30 |
| 5 | 30 | 30 |
| 10 | 60 | 30 |
| 10 | 0 | Lipofectin™ |

EXAMPLE 12

SK-BR-3, Caco-2, Caov-3 and MCF7 cells were transfected with ODN1 using 34 which was prepared as described in Example 5 using a 1:1 molar ratio of DOPE colipid. The sonicated lipid-colipid mixture (1 mL of a 2.5, 5 or 10 μg/mL suspension) was mixed with 250 pmole ODN1 and allowed to stand for 15 minutes at room temperature for 15 minutes before adding 1 mL of the lipid-ODN1 complex to the cells. The lipid-ODN1 complex was removed from the cells after 6 hours by washing the cells twice in PBS, followed by observing the cells in serum-containing medium immediately after removing the lipid-ODN1 complex.

| | μg lipid | % transfected | toxicity* |
|---|---|---|---|
| Caco-2 | 2.5 | <5 | — |
| | 5.0 | 10–15 | + |
| | 10.0 | 0 | +++ |
| Caov-3 | 2.5 | 20 | — |
| | 5.0 | 20 | — |
| | 10.0 | 61 | + |
| MCF7 | 2.5 | 30–50 | — |
| | 5.0 | 83 | — |
| | 10.0 | 80 | ± |
| SK-BR-3 | 2.5 | 60–70 | — |
| | 5.0 | >90 | — |
| | 10.0 | >90 | + |

*(−), no observed toxicity; (±), slight toxicity with no dead cells apparent, (+), moderate toxicity with <10% dead cells, (+++), all cells dead

EXAMPLE 13

The optimal molar ratio of cationic lipid:colipid was determined using 34 and DOPE colipid. 34 and DOPE in CHCl₃ were mixed to obtain various molar ratios of the 2 lipids. The lipids were dried under vacuum, resuspended in deionized water by 10 freeze-thaw cycles, and filtered through a 100 nm Lipofast™ filter (Avestin, Inc.) according to manufacturers instructions to obtain a lipid suspension consisting of particles less than about 100 nm in diameter. CV-1 cells were transfected for 24 hours using 1 mL of 10 μg/mL lipid and 250 pmole ODN2 and observed immediately after removing the transfection mixture by washing twice with DMEM containing 10% FBS. The efficiency of ODN2 transfection into the cells increased steadily from a 80–90% transfection efficiency at a 34:DOPE ratio of 1:2.5 to a very high efficiency (~100%) at a 2.5:1 ratio. The transfection efficiency with respect to the amount of ODN1 delivered into cells was highest for the 2.5:1 transfection based on a qualitative estimate of the fluorescence intensity observed in the cells after transfection. The transfection efficiency of the 34:DOPE (1:2) preparation delivered about the same amount of oligonucleotide to CV-1 cells as Lipofectin™ when used according to manufacturer's instructions. No toxicity or slight toxicity was observed after transfection with the tested preparations.

| 34:DOPE molar ratio | % transfected |
|---|---|
| 1:2.5 | 80–90 |
| 1:2 | >95 |
| 1:1.5 | >95 |
| 1:1 | >95 |
| 1.5:1 | >95 |
| 2:1 | >95 |
| 2.5:1 | >95 |

EXAMPLE 14

The transfection efficiency of 34 was compared with Lipofectin™ and Transfectam™ (Promega, No. E1231) by determining the proportion of transfected cells as observed by fluorescence using ODN-1. Transfection preparations were as follows: #1 was 34 cationic lipid with DOPE colipid (1:1 molar ratio); #2 was Lipofectin™ with DOPE (1:1 molar ratio); #3 was Transfectam™ without colipid; #4 was Transfectam™ with DOPE (1:1 molar ratio). The cells were transfected for 6 hours using 5 μg of lipid with 250 pmole of ODN-1 and viewed immediately after the cells were washed.

| transfection | cell line | | | | |
|---|---|---|---|---|---|
| | ECL | CV-1 | MCF7 | SK-BR-3 | RAT-2 |
| #1 A* | 88 | >95 | 41 | 44 | >95 |
| #1 B | 15 | >95 | 81 | 53 | >95 |
| #2 A | 0–5 | >95 | 49 | 27 | 95 |
| #2 C | 0–5 | 47 | 50 | 20 | 24 |
| #3 A | 0–5 | 16 | 0–5 | 0 | 0–5 |
| #3 C | 0 | 0–5 | 0–5 | 0 | 0 |
| #4 A | 0 | 30 | 0–5 | 0–5 | 25 |
| #4 C | 0 | 22 | 10 | 0 | 21 |

*- A transfection in Optimem ™ without serum; B - transfection in DMEM with 15% FBS; C - transfection in DMEM with 10% FBS.

The transfection efficiency of 34 was also compared to that obtained using Lipofectin™ and Transfectam™ by measuring the transfection efficiency (ODN2) in CV-1 cells using transfection times from 2 to 24 hours. Transfection preparations #1–#4 were used in medium containing 10% FBS and gave the following results.

| transfection | transfection time (hours) | | | |
|---|---|---|---|---|
| | 2 | 4 | 6 | 24 |
| #1 | 89 | >95 | >95 | >95 |
| #2 | 85 | >95 | 47 | >95 |
| #3 | 13 | 39 | 0–5 | 80 |
| #4 | 12 | 19 | 22 | 27 |

The reduced efficiency of transfection with Lipofectin™ at the 6 hour time point was probably due to transfection of cells that were at about 90–95% confluency, which was more confluent than the 70–80% confluency recommended by the manufacturer. Relatively low cell toxicity was observed in all of the transfections (0–10% dead cells observed after transfection) except with transfection #3 at 24 hours, where about 50% of the cells were dead.

Transfection preparations #1 and #2 were used to transfect CV-1 cells for 6 hours as described except that the transfection medium contained either 25% FBS or 50% FBS. #1 transfected >95% of CV-1 cells in medium containing 25% FBS and 71% in 50% FBS while #2 transfected 21% of the cells in 25% FBS and 0–5% in 50% FBS. The transfection efficiency using 34 in the presence of high levels of serum was thus relatively high.

EXAMPLE 15

CV-1 cells were transfected with a different molar ratios of 35 and DOPE colipid for 24 hours using 250 pmole of ODN2 and 1 μg of lipid-colipid complex per 1 mL transfection. DMEM with 10% FBS was used in the transfection preparations. 35 was found to transfect about 2- to 10-fold more oligonucleotide into transfected cells than 34 at all tested lipid:colipid ratios.

No toxicity or slight toxicity (less than about 5% dead cells after transfection) was observed after transfection with the tested preparations.

| 35:DOPE molar ratio | % transfected |
|---|---|
| 1:1 | >95 |
| 1.5:1 | >95 |
| 2:1 | >95 |
| 2.5:1 | >95 |
| 3:1 | 90 |
| 5:1 | 70–90 |

35 was tested as a 2:1 35:DOPE preparation using 0.5, 1 or 2.5 μg of lipid per 1 mL transfection (CV-1 cells transfected for 24 hours using 250 pmole ODN2). Greater than 95% of the cells were transfected at all 3 lipid concentrations, although the amount of oligonucleotide delivered into cells was reduced by about 10-fold in the transfection using 0.5 μg of lipid preparation relative to the transfections that used 1.0 or 2.5 μg of lipid. No toxicity or slight toxicity (less than about 5% dead cells after transfection) was observed after transfection with the tested preparations.

EXAMPLE 16

CV-1 cells were transfected for 24 hours with RNA encoding chloramphenicol acetyltransferase (CAT). The transfections used 2.5 μg of RNA, 5 μg of 34 and DMEM with 10% FBS or Optimem™ with no serum. CAT activity was measured by immunofluorescence staining using fluorescent labeled anti-CATantibodies (5',3' Inc.). The cells were observed as previously described (Wagner, *Science*

(1993) 260:1510). The results showed 1–2% of cells expressed CAT while no control cells transfected with lipid lacking RNA expressed CAT.

EXAMPLE 17

Transfection preparations #5 (35 and DOPE at a 1:1 molar ratio; 5 µg lipid complex), #6 (5 µg 34 without DOPE colipid), #7 (43 and DOPE at a 1:1 molar ratio; 5 µg lipid complex) and #8 (42 and DOPE at a 1:1 molar ratio; 5 µg lipid complex) were used to transfect CV-1 cells for 48 hours using 250 pmole ODN2. Cells were observed by immunofluorescence immediately after removing the transfection lipids. Transfection #5 resulted in >95% of cells transfected and no visible toxicity, with a very high fluorescence intensity in nearly all nuclei, indicating that high levels of ODN2 were delivered into the cells. Transfection #6 similarly resulted in >95% of cells transfected and no visible toxicity. Transfections #7 and #8 resulted in 44% and 32% of cells transfected respectively, with no visible toxicity.

EXAMPLE 18

Two plasmid DNAs, one encoding the CAT enzyme (Invitrogen, No. V790-20) and the other encoding β-galactosidase (Clontech, No. 6177-1), were transfected into cells in Swiss Webster mice by injecting 50 µL of lipid-plasmid complex intradermally, followed by assaying for CAT and β-galactosidase activity at the site of injection 2 days after injection. The transfection preparations consisted of lipid-nucleic acid complexes as follows:

9, 20 µg of a 1:1 34:DOPE complex with 0.5 µg of each plasmid DNA in 1 mL of Optimem™ without serum;

10, 20 µg of a 1:1 34:DOPE complex with 1.5 µg of each plasmid DNA in 1 mL of Optimem™ without serum;

11, 20 µg of Lipofectin™ with 0.5 µg of each plasmid DNA in 1 mL of Optimem™ without serum;

12, 20 µg of Lipofectin™ with 1.5 µg of each plasmid DNA in 1 mL of Optimem™ without serum;

13, 20 µg of DC-cholesterol with 0.5 µg of each plasmid DNA in 1 mL of Optimem™ without serum;

14, 20 4µg of DC-cholesterol with 1.5 µg of each plasmid DNA in 1 mL of Optimem™ without serum; and

15, 20 4µg/mL of a 1:1 34:DOPE complex with no plasmid DNA in 1 mL of Optimem™ without serum.

Transfection preparations containing 34 were complexed with the plasmids for 15 to 30 minutes prior to intradermal injection. DC-cholesterol (3-β-[N-(N',N'-dimethylaminoethane)carbamyl]cholesterol) was prepared and used as described (Gao Biochem Biophys Res Commun (1991) 179:280). A 6 mm diameter biopsy of epidermis and dermis was removed from the mice at each injection site. The tissue from each site was homogenized in 0.25M Tris pH 7.4, 0.1% Triton X-100, centrifuged and the tissue pellet used to prepare a 150 µL cell extract essentially as described (Gorman Mol Cell Biol (1982) 2:1044). The cell extracts were assayed for CAT and β-galactosidase activity according to published methods (Gorman, ibid.; Miller Experiments in Molecular Genetics (1972) CSH press, p 352). β-galactosidase activity was measured using a fluorimeter to measure conversion of 4-methylumbelliferyl-β-D-galactopyranoside to the flourescent derivative 4-methylumbelliferone (Prince Proc Natl Acad Sci (1987) 84:156). The error inherent in the assay due to variation in the protein concentrations of the cell extracts was estimated to be less than about ±15%. No signs of toxicity were visually observed at the injection site with any of the transfection preparations. The following results were obtained.

| transfection | CAT* | β-galactosidase** |
|---|---|---|
| #9 | 0.9 | 100.3 |
| #10 | 2.1 | 172.5 |
| #11 | 0.3 | 121.0 |
| #12 | 0.3 | 75.0 |
| #13 | 0.7 | 112.0 |
| #14 | 0.4 | 79.9 |
| #15 | 0.0 | 80.0 |

*- percent acetylation of $^{14}$C labeled chloramphenicol using 50 µL of cell extract
**- fluorescene units using 50 µL of cell extract Similar methods can be used to transfect oligonucleotides into cells in animals. For example, inhibiting gene expression using an antisense oligonucleotide in cells can be shown by adding an oligonucleotide having a base sequence complementary to CAT or β-galactosidase to a transfection preparation such as #9 or #10. Inhibition of gene expression is then measured by determining the expression of the gene in the presence of oligonucleotide compared to expression that is obtained using transfection preparations lacking antisense oligonucleotide. The nontargeted gene is used as an internal control to detect nonspecific inhibition of transcription that may be caused by the oligonucleotide.

EXAMPLE 19

ODN2A, which was ODN2 lacking the fluorescent label at the 3' terminus, was used as an antisense oligonucleotide to inhibit T antigen expression in CV-1 cells using the protocol previously described (Wagner Science (1993) 260:1510–1513). CV-1 cells were transfected for 18 hours using 5 µg of 34 (1:1 molar ratio with DOPE colipid) and then cell nuclei were microinjected with T antigen plasmid using a needle concentration of 0.003 µg/mL of T antigen plasmid (ibid at page 1513, first column, note 5) and 0.025 µg/mL of β-galactosidase plasmid. The cells were scored for T antigen expression 4.5 hours after removing the transfection preparation from the cells. The cells were immunostained for β-galactosidase expression as an internal control for microinjected cells and the proportion of cells expressing both T antigen and β-galactosidase was determined. This manner of inhibiting gene expression using this oligomer was previously observed (Wagner, ibid) and 34 thus did not affect the nature of the biological activity previously observed with ODN2A. The results showed that transfection preparations containing 34 efficiently delivered the antisense oligomer into the cells without interfering with the capacity of the oligonucleotide to inhibit gene (protein) expression by binding to the target RNA sequence in the cell. Transfection using 34 compared to transfection using Lipofectin™ indicated that 34 was about 10-fold more efficient in delivering ODN2A into the cells (i.e., about 10-fold less ODN2A was needed to inhibit T antigen expression to an equal extent).

EXAMPLE 20

Lipid complexes consisting of 35:DOPE (2:1 molar ratio) were prepared as follows. Two molar equivalents of 35 in $CHCl_3$ and one equivalent of DOPE in $CHCl_3$ was dried under reduced pressure by rotovap at room temperature. Deionized water was then added to give 1 mg/mL of total lipid. 10 mL of water containing 10 mg of lipid was vortexed for 5 minutes in a 100 mL round bottom flask. 2 mL aliquots were then used to prepare lipid suspensions for complexing with ODN1. The first preparation was obtained by directly using the vortexed 2 mL aliquot to prepare complexes with ODN1. The second preparation was obtained by 6 cycles of freezing on dry ice and thawing in a 37° C. water bath (Baxter, Dura Bath). The third preparation was obtained by placing a culture tube containing the lipid into a Ultra Sonik 100 (NEY) sonicator and the preparation was sonicated for 30 minutes at room temperature using the probe tip at maximum power. The fourth preparation was obtained by 6 cycles of freezing on dry ice and thawing in a 37° C. water bath, followed by filtering the suspension through a Lipofast™ 100 nm filter according to the manufacturer's instructions to obtain complexes less than about 100 nm in diameter. The fifth preparation was obtained by sonication for 10 minutes in a sonication bath followed by 5 sonication pulses for 15 seconds each with a probe sonicator (Sonifier 250, Branson Ultrasonics). Each preparation was used to transfect CV-1 cells for 6 hours using 1 μg lipid and 250 nmole ODN1 in 1 mL of medium with 10% FBS. All preparations efficiently transfected CV-1 cells, with some variation observed in the amount of ODN1 delivered to cells and/or some variation in the proportion of cells that were transfected.

We claim:

1. A composition comprising nucleopolymer and a lipid having the structure A

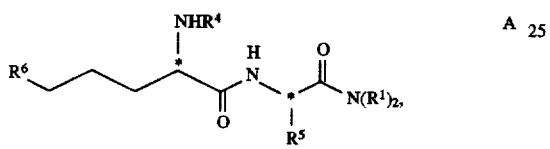

or a salt or solvate thereof wherein each $R^1$ is alkyl (12–22 C) or mono unsaturated alkenyl (12–22 C);

$R^4$ is H;

$R^5$ is H, $CH_3$, $CH(CH_3)_2$, $CH_2CH(CH_3)_2$, $CH(CH_3)CH_2CH_3$, $CH_2C_6H_5$, $CH_2C_6H_4OH$, $CH_2OH$, $CH(OH)CH_3$, $(CH_2)_4NHR^4$, $(CH_2)_3NHR^4$ or $(CH_2)_3NR^4C(NH)NHR^4$; and $R^6$ is $NHR^4$, $CH_2NHR^4$ or $NR^4C(NH)NHR^4$.

2. The composition of claim 1 wherein the nucleopolymer comprises an expression vector capable of expressing a polypeptide in a cell.

3. The composition of claim 2 wherein the polypeptide is a histocompatibility antigen, cell adhesion molecule, cytokine, antibody, antibody fragment, cell receptor subunit, cell receptor, intracellular enzyme or extracellular enzyme.

4. The composition of claim 1 wherein the nucleopolymer is an oligonucleotide.

5. The composition of claim 1 wherein $R^5$ is H.

6. The composition of claim 1 wherein each $R^1$ is independently —$(CH_2)_{19}CH_3$, —$(CH_2)_{17}CH_3$, —$(CH_2)_{15}CH_3$, —$(CH_2)_{13}CH_3$, —$(CH_2)_{11}CH_3$, —$(CH_2)_5[z]CH=CH(CH_2)_7CH_3$ or —$(CH_2)_8[z]CH=CH(CH_2)_7CH_3$.

7. The composition of claim 6 wherein $R^5$ is H.

8. A compound having the structure

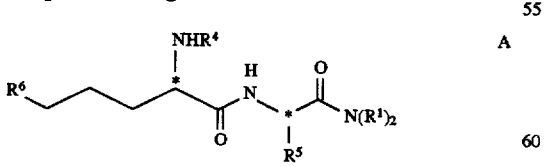

or a salt or solvate thereof wherein each $R^1$ independently is alkyl (12–22 C) or mono unsaturated alkenyl (12–22 C);

$R^4$ is H or a protecting group;

$R^5$ is H, $CH_3$, $CH(CH_3)_2$, $CH_2CH(CH_3)_2$, $CH(CH_3)CH_2CH_3$, $CH_2C_6H_5$, $CH_2C_6H_4OH$, $CH_2OH$, $CH(OH)CH_3$, $(CH_2)_4NHR^4$, $(CH_2)_3NHR^4$ or $(CH_2)_3NR^4C(NH)NHR^4$; and $R^6$ is $NHR^4$, $CH_2NHR^4$ or $NR^4C(NH)NHR^4$.

9. The compound of claim 8 wherein each $R^1$ is —$(CH_2)_{19}CH_3$, —$(CH_2)_{17}CH_3$, —$(CH_2)_{15}CH_3$, —$(CH_2)_{13}CH_3$, —$(CH_2)_{11}CH_3$, —$(CH_2)_5[z]CH=CH(CH_2)_7CH_3$ or —$(CH_2)_8[z]CH=CH(CH_2)_7CH_3$.

10. The compound of claim 8 wherein $R^4$ is H or a protecting group and $R^5$ is H.

11. The compound of claim 10 wherein the protecting group is t-BOC.

12. The compound of claim 11 wherein each $R^1$ independently is —$(CH_2)_{19}CH_3$, —$(CH_2)_{17}CH_3$, —$(CH_2)_{15}CH_3$, —$(CH_2)_{13}CH_3$, —$(CH_2)_{11}CH_3$, —$(CH_2)_5[z]CH=CH(CH_2)_7CH_3$ or —$(CH_2)_8[z]CH=CH(CH_2)_7CH_3$.

13. The compound of claim 12 having the structure

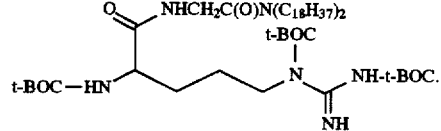

14. The compound of claim 12 having the structure

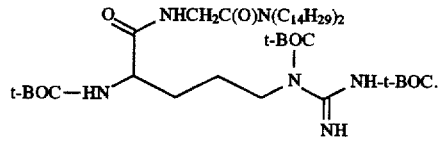

15. The compound of claim 10 wherein $R^4$ is H.

16. The compound of claim 15 wherein each $R^1$ independently is —$(CH_2)_{19}CH_3$, —$(CH_2)_{17}CH_3$, —$(CH_2)_{15}CH_3$, —$(CH_2)_{13}CH_3$, —$(CH_2)_{11}CH_3$, —$(CH_2)_5[z]CH=CH(CH_2)_7CH_3$ or —$(CH_2)_8[z]CH=CH(CH_2)_7CH_3$.

17. The compound of claim 16 having the structure

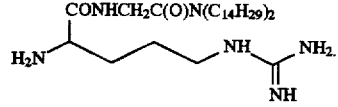

18. The compound of claim 16 having the structure

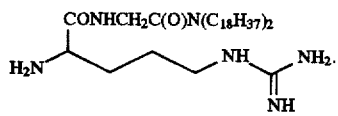

19. The compound of claim 17 and a colipid in a mixture.

20. The colipid of claim 19 wherein the colipid is DOPE.

* * * * *

UNITED STATES PATENT AND TRADEMARK OFFICE
CERTIFICATE OF CORRECTION

PATENT NO. : 5,777,153
DATED : July 7, 1998
INVENTOR(S) : Kuei-Ying Lin, et al.

It is certified that error appears in the above-identified patent and that said Letters Patent is hereby corrected as shown below:

On the title page, item [56], insert the following:

U. S. PATENT DOCUMENTS

| EXAMINER INITIAL | | PATENT NUMBER | | | | | | ISSUE DATE | PATENTEE | CLASS | SUBCLASS | FILING DATE IF APPROPRIATE |
|---|---|---|---|---|---|---|---|---|---|---|---|---|
| | | 4 | 8 | 6 | 3 | 9 | 0 | 5 | 9/5/89 | Hudspeth et al. | | | |
| | | | | | | | | | | | | | |

Signed and Sealed this

Sixteenth Day of February, 1999

Attest:

Attesting Officer

*Acting Commissioner of Patents and Trademarks*